United States Patent
Troy

(10) Patent No.: US 11,471,731 B1
(45) Date of Patent: Oct. 18, 2022

(54) PERFORMANCE IMPROVEMENT SYSTEM

(71) Applicant: Gregory Troy, Los Angeles, CA (US)

(72) Inventor: Gregory Troy, Los Angeles, CA (US)

( * ) Notice: Subject to any disclaimer, the term of this patent is extended or adjusted under 35 U.S.C. 154(b) by 912 days.

(21) Appl. No.: 16/263,059

(22) Filed: Jan. 31, 2019

(51) Int. Cl.
*A63B 24/00* (2006.01)
*A63B 71/06* (2006.01)
*A41D 19/00* (2006.01)

(52) U.S. Cl.
CPC ...... *A63B 24/0062* (2013.01); *A41D 19/0027* (2013.01); *A63B 71/0622* (2013.01); *A63B 2071/063* (2013.01); *A63B 2220/62* (2013.01); *A63B 2220/836* (2013.01); *A63B 2230/04* (2013.01)

(58) Field of Classification Search
CPC ................. A63B 24/00; A41D 19/00
See application file for complete search history.

(56) References Cited

U.S. PATENT DOCUMENTS

| | | | |
|---|---|---|---|
| 8,572,764 B2 | 11/2013 | Thellmann | |
| 2016/0256082 A1* | 9/2016 | Ely | A61B 5/0024 |
| 2016/0324432 A1* | 11/2016 | Ahmed | A61B 5/0255 |
| 2017/0086519 A1* | 3/2017 | Vigano' | A63B 71/141 |
| 2017/0100632 A1* | 4/2017 | Castelo Branco | A61B 5/1114 |
| 2017/0225032 A1* | 8/2017 | Jones | A61B 5/1114 |
| 2018/0345078 A1* | 12/2018 | Blahnik | A61B 5/742 |

\* cited by examiner

*Primary Examiner* — Eugene L Kim
*Assistant Examiner* — Christopher Glenn
(74) *Attorney, Agent, or Firm* — Sanchelima & Associates, P.A.; Christian Sanchelima; Jesus Sanchelima

(57) ABSTRACT

The present invention is disclosing a performance improvement system comprising a smart athletic flexible accessory and an electronic device communicably coupled with smart athletic flexible accessory. Smart athletic flexible accessory comprises a plurality of fabric sensors configured to measure data associated with a physical activity performed by a user and a first transceiver configured to transmit measured data. Electronic device comprises a second transceiver configured to receive measured data from smart athletic flexible accessory, and a microprocessor. Microprocessor is configured to analyze received data from receiver, generate a recommendation based on analyzed data, and cause a display screen to display generated recommendation.

10 Claims, 3 Drawing Sheets

PERFORMANCE IMPROVEMENT SYSTEM

BACKGROUND OF THE INVENTION

1. Field of the Invention

The present disclosure relates to a performance improvement system. More particularly, the present disclosure relates to a performance improvement system for users performing physical activities.

2. Description of the Related Art

Many systems are available for measuring performance of a user doing a physical activity. User may be a fitness enthusiast, an athlete, a sports person, or a construction worker. For example, electronic gloves comprising sensors may detect usage data, such as amount of weight lifted by user. The usage data may be automatically generated and downloaded to a central computer system and made available for the user's review.

Several designs of performance improvement systems have been presented in the past. None of them, however, presents an efficient and simple system that analyzes usage data and accordingly generates recommendations to improve the performance of the user.

Applicant believes that a related reference corresponds to U.S. Pat. No. 8,572,764 by Dieter Thellmann that discloses a glove body, which comprises a glove body internal surface that defines a palm compartment enveloping at least part of a user's palm, a glove body external surface, and a wrist aperture that provides an opening for the user's hand. Digit appendages comprise a digit appendage internal surface that extends the palm compartment to envelop all/part of the user's digit, and a digit appendage external surface. One or more sensors are attached to the glove body to detect one or more hand exercise events that involve a user hand exercise. A memory component, powered by a battery, stores the hand exercise event, upon receiving a hand exercise event detected by a sensor. A device interface delivers the one or more hand exercise events from the memory to a device, upon connection to the device. However, there is not disclosed that the device further provides recommendations for improving performance of user performing physical activities.

Other documents describing the closest subject matter provide for a number of more or less complicated features that fail to solve the problem in an efficient and economical way. None of these patents suggest the novel features of the present invention.

SUMMARY OF THE INVENTION

It is an object of the present invention to provide a performance improvement system. Performance improvement system may comprise a smart athletic flexible accessory and an electronic device communicably coupled with smart athletic flexible accessory. Smart athletic flexible accessory may comprise a plurality of fabric sensors configured to measure data associated with a physical activity performed by a user, and a first transceiver configured to transmit measured data. Electronic device may comprise a second transceiver configured to receive measured data from smart athletic flexible accessory, and a microprocessor. Microprocessor may be configured to analyze said received data from said receiver, generate a recommendation based on said analyzed data, and cause a display screen to display generated recommendation. In various examples, user may be a construction worker, an athlete, an amateur, or a person doing a workout. In various examples, smart athletic flexible accessory may be a glove, a half finger glove or a without finger glove, embedded with plurality of fabric sensors.

In accordance with various embodiments, measured data may correspond to a measure of a weight that is being lifted and a lowering magnitude, a time duration for which weight is kept static, a cadence for each repetition and an average for a plurality of repetitions for physical activity, and an average lifting time duration on each repetition of physical activity. In accordance with an embodiment, measured data may be utilized to compensate cadence, resistance, lowering, and angle correction for physical activity for optimal training purpose.

Generated recommendation may correspond to one or more alternative physical activities that can be performed by user. Smart athletic flexible accessory further may comprise a program to identify physical activity and adjust measured data associated with physical activity performed by user. Program may further indicate total weight lifted during each physical activity during each session. Program may further indicate grip strength and point of failure of grip strength. Generated recommendation may facilitate improved grip strength, and an amount of time doing positive and negative.

In accordance with an embodiment, smart athletic flexible accessory may further comprise a feedback circuitry configured to provide a feedback to user to perform additional repetitions when user is unable to perform another repetition.

In accordance with an embodiment, microprocessor may be further configured to analyze additional repetitions, generate a new recommendation, and cause display screen to display generated new recommendation.

Further objects of the invention will be brought out in the following part of the specification, wherein detailed description is for the purpose of fully disclosing the invention without placing any limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
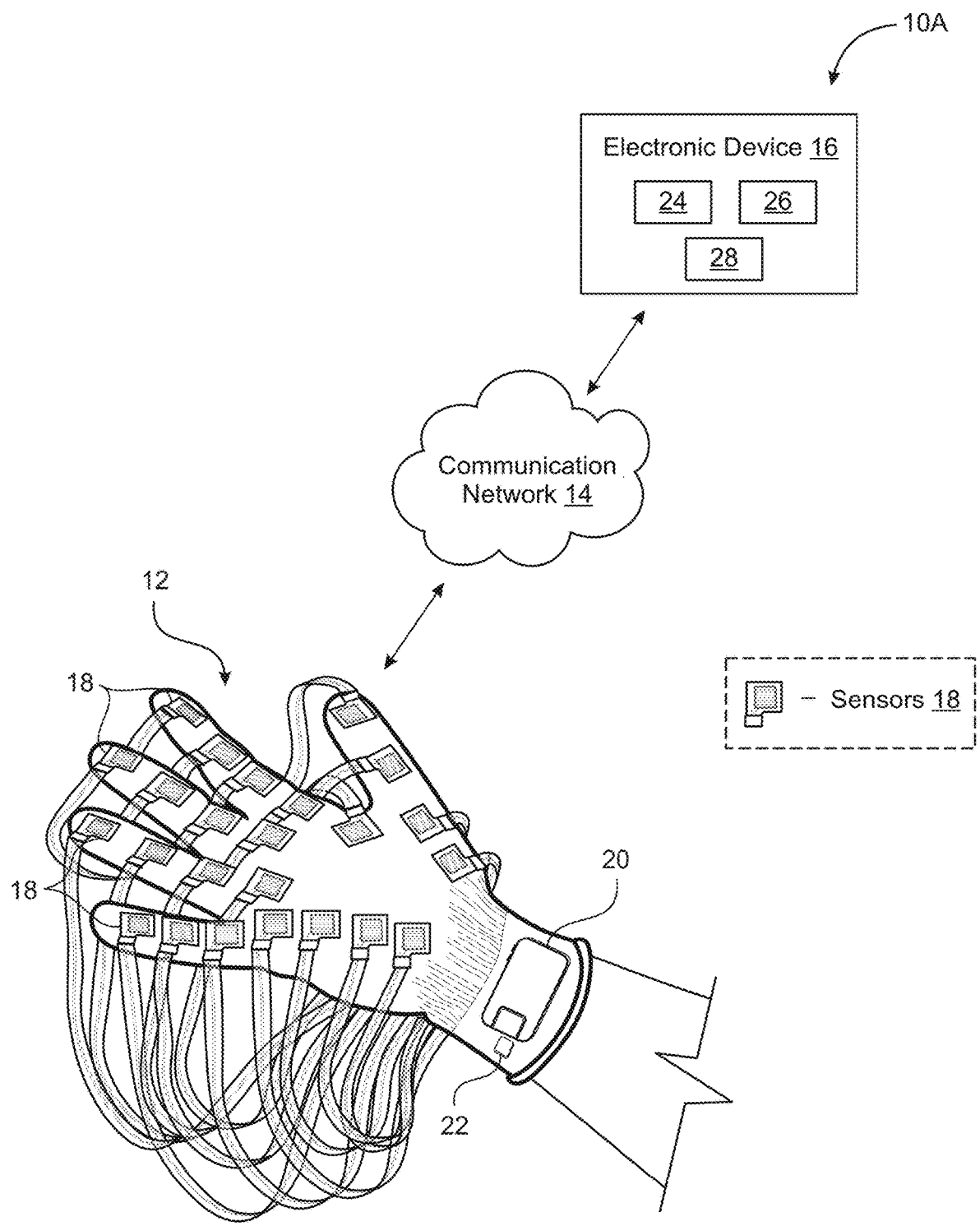
FIGS. 1 and 1A represent performance improvement systems 10A and 10B of present invention, according to two embodiments described herein.

Referring now to the drawings, FIGS. 1-2A, where the present invention is generally referred to with numerals 10A and 10B, it can be observed that a performance improvement system, in accordance with one embodiment, is provided that includes various components, a described hereinafter.

Figure 1A:
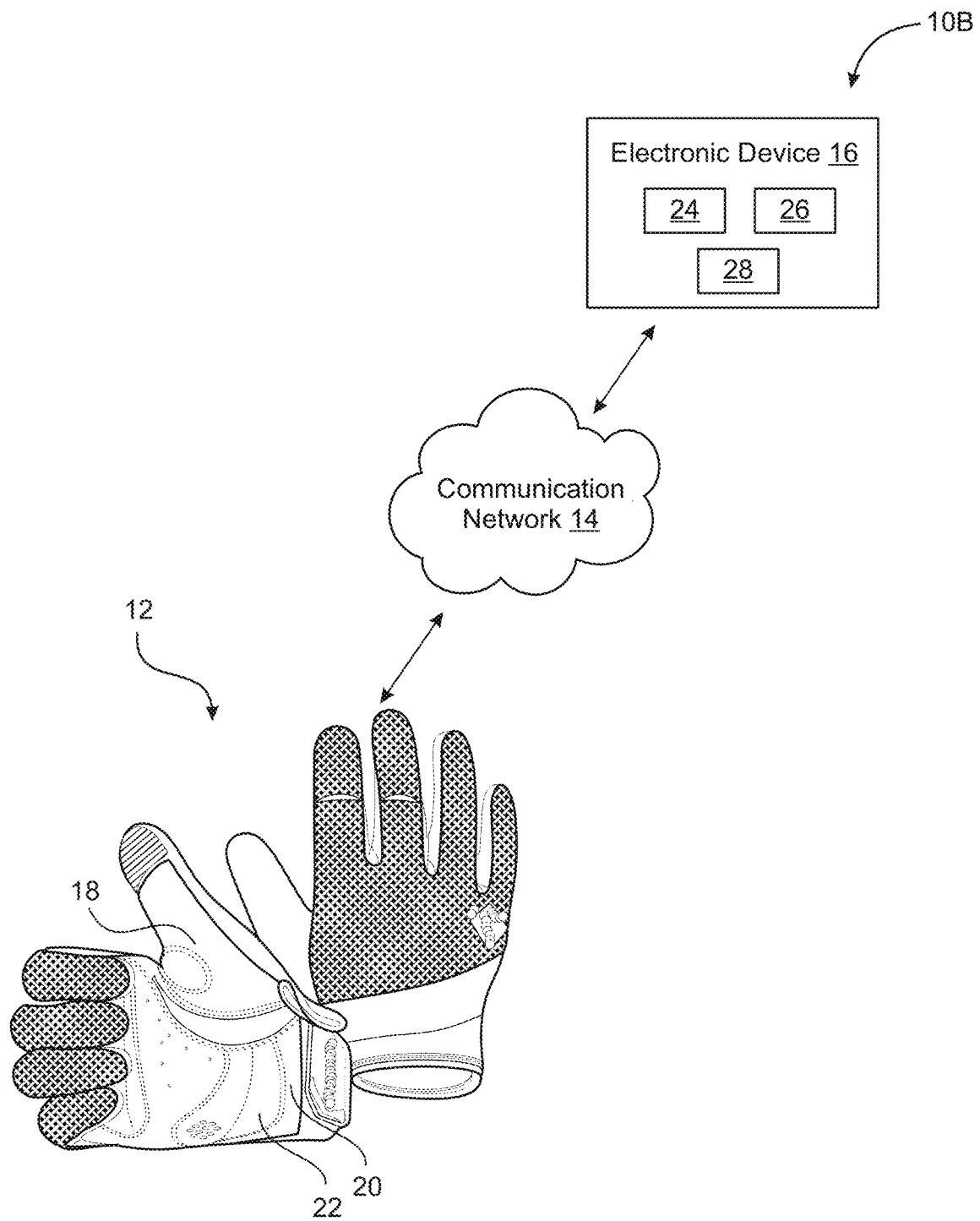

FIGS. 1 and 1A represent performance improvement systems 10A and 10B of present invention, according to various embodiments described herein. Performance improvement systems 10A and 10B depict two different designs of a smart athletic flexible accessory 12 according to two embodiments. mart athletic flexible accessory 12 may be communicably coupled with an electronic device 16 via a communication network 14. Smart athletic flexible accessory 12 may comprise a plurality of fabric sensors 18, a rechargeable battery 20, and a first transceiver 22. Electronic device 16 may further comprise a second transceiver 24, a microprocessor 26, and input/output (I/O) devices 28.

Smart athletic flexible accessory 12 may correspond to one of a glove, a half finger glove or a without finger glove, embedded with plurality of fabric sensors 18. Glove may comprise a glove body including a glove body internal surface that defines a palm portion enveloping at least a portion of a palm of user. Glove body may further comprise a glove body external surface and a wrist aperture, such as for inserting user's hand. Finger appendages i.e. finger portions may comprise a finger appendage internal surface that extends palm portion to envelop fingers of user. Five finger appendages may further comprise a finger appendage external surface. It may be noted that only palm portion extended to five digit appendages may be embedded with plurality of fabric sensors 18.

Electronic device 16 may correspond to a device capable for processing data received from external devices, for example smart athletic flexible accessory 12. Electronic device 16 may analyze data from first transceiver, generate a recommendation based on analyzed data, and display generated recommendation. Examples of electronic device 16 may include, but not limited to, a desktop, a laptop, a tablet, or the like.

Communication network 14 may correspond to a network that may facilitate a communication between various devices, for example smart athletic flexible accessory 12 and electronic device 16, in performance improvement systems 10A and 10B. In accordance with various embodiments, communication network 14 may be a wired network or a wireless network.

Plurality of fabric sensors 18 may include, for example contact sensor, proximity sensor, motion sensor, biometric sensor, or pressure sensor, which may be configured to measure data associated with a physical activity performed by user and generate a signal. Plurality of fabric sensors 18 may be configured to count repetitions of movement (i.e. how many times wearer swung a golf club and how hard he hits the ball for a day or any time frame how many pushups wearer did, how much weight wearer lifted, and the like). Plurality of fabric sensors 18 may be further configured to determine a range of motion for each athletic or work task wearer performs and stores date related to range of motion of wearer and can make suggestions on range of motion Plurality of fabric sensors 18 may be configured to weigh a load that wearer is holding (for example, wearer holds ten pounds in hand, and readout on associated smart phone shows ten pounds). It can also multiply the weight by your lowering speed and show you how much the weight actually is when lowered slowly versus dropped or lowered quickly Plurality of fabric sensors 18 may be configured to determine heart rate of wearer at all times during wearing and records such data for cross reference to time under stress while working and can make recommendations during concerning training heart range and maximum heart range of the current wearer.

Plurality of fabric sensors 18 may be configured to vibrate to instruct wearing of proper cadence to lower resistance (for example, when lifting weights or doing pushups). Plurality of fabric sensors 18 may be further configured to guide wearer to accentuate to eccentric contraction or lowering portion, thereby suggesting wearer to lift in one beat and lower in four beats, for example. Plurality of fabric sensors 18 may be further configured to be a standalone device with a screen on either wrist or be solely to connect to an Android or a smartphone. An app corresponding to the performance management system may instruct for lifting weights or more accurately resistance exercise to be followed. For such utility, the app with associated program may be installed in a smart device associated with smart athletic flexible accessory 12. Plurality of fabric sensors 18 may be further configured to produce data about Cadence or Rhythm of wearer. Lowering time coupled with heart rate and range of motion may allow program to make real time changes based on current health of wearer and how wearer feels and make suggestions to improve performance. Wearer may go easy or go hard. Accordingly program may detect weaknesses of wearer and improve through progressive resistance training. Such measured data may be transmitted by first transceiver 22 to electronic device 16, via communication network 14 Wearer can also be monitored for health problems such as a construction worker or a pilot or a member of the space force for how much work they are doing and how it is affecting performance.

Rechargeable battery 20 may be configured to provide power to plurality of electronic and electrical components, such as plurality of fabric sensors 18 and first transceiver 22, of smart athletic flexible accessory 12. In an embodiment, rechargeable battery 20 may be charged from an external power supply via a power cable (not shown). In an embodiment, rechargeable battery 20 may be lithium-ion batteries that are small, durable, and having long life. Alternatively, rechargeable battery 20 may be recharged when power level drops below a threshold power level.

First transceiver 22 and second transceiver 24 may correspond to a communication means in smart athletic flexible accessory 12 through which smart athletic flexible accessory 12 may be configured to communicate with electronic device 16, via communication network 14.

Microprocessor 26 may be configured to perform analysis of measured data, and generate recommendations, and cause output device, such as display screen, of I/O devices 28, to display generated recommendation. Microprocessor 26 may be an X86-based processor, a Reduced Instruction Set Computing (RISC) processor, an Application-Specific Integrated Circuit (ASIC) processor, a Complex Instruction Set Computing (CISC) processor, a microcontroller, a central processing unit (CPU), a digital signal processor (DSP), a graphics processor unit (GPU), a coprocessor, and/or other processors or integrated circuits.

I/O devices 28 may include a set of input and output devices that may be configured to provide input and generate output, respectively. For example, set of input devices may include a keyboard or touchscreen and output devices may include a display screen and a voice such as a British Butler or a Boxing coach.

In operation, plurality of fabric sensors 18 may be configured to measure data associated with a physical activity performed by a user. For example, when user is a fitness enthusiast, measured data may correspond to amount and duration of weights lifted up or down during each repetition of exercising. In another example, when user is a construction worker, measured data may correspond to amount and duration of load lifted up or down during loading or unloading.

In accordance with various embodiments, measured data may correspond to a measure of a weight that is being lifted and a lowering magnitude, a time duration for which weight is kept static, a cadence for each repetition and an average for a plurality of repetitions for physical activity, and an average lifting time duration on each repetition of physical activity. In accordance with an embodiment, measured data may be utilized to compensate cadence, resistance, lowering, and angle correction for physical activity for optimal training purpose.

In other words, smart athletic flexible accessory 12 may measure how much weight user is lifting and then how much user is lowering, how long user has kept weight static, cadence for each repetition, and an average for all repetitions for each exercise. Smart athletic flexible accessory 12 may further provide details of how long user was lifting weights for on average and on each repetition of exercise. Further, measured data may be used to make corrections to cadence, resistance, lowering, and angle of exercise for optimum training purposes.

First transceiver 22 may be configured to transmit measured data to second transceiver 24 of electronic device 16 via communication network 14. Second transceiver 24 in electronic device may 16 may be configured to receive measured data from first transceiver 22 and communicate measured data to microprocessor 26. Microprocessor 26 may be configured to analyze received data and generate a recommendation based on analyzed data. Microprocessor 26 may be configured to cause a display screen in I/O devices 28 to display generated recommendation. Generated recommendation may correspond to one or more alternative physical activities that can be performed by user.

In accordance with an embodiment, smart athletic flexible accessory 12 may comprise a program to identify physical activity, for example exercise, and adjust measured data associated with physical activity performed by user. Program may further indicate total weight lifted during each physical activity, for example exercise, during each session, for example workout. Program may further indicate grip strength and point of failure of grip strength. Generated recommendation may facilitate improved grip strength, and an amount of time doing positive and negative. In accordance with an embodiment, smart athletic flexible accessory 12 may further comprise a feedback circuitry configured to provide a feedback to user to perform additional repetitions when user is unable to perform another repetition. For example, smart athletic flexible accessory 12, for example gloves, may give a shock to user through electric stimulation when user can no longer do another repetition to make user do, for example three more. In accordance with an embodiment, microprocessor 26 may be further configured to analyze additional repetitions, such as three repetitions in above example, generate a new recommendation, and cause display screen to display generated new recommendation on, for example a phone, a watch or a laptop in real time. In other words, performance improvement systems 10A and 10B make recommendation to user's training to suggest another way to train that is more beneficial to user.

In accordance with an embodiment, smart athletic flexible accessory 12 may act as a personal trainer for wearer and may be adjust to any voice wearer wants. Smart athletic flexible accessory 12 may be battery powered through induction charging. An hour and a half charge may be fine for exercise, but working people doing activities other than training may need a longer charging. Smart athletic flexible accessory 12 may have one of Bluetooth or cord capability. In accordance with an embodiment, smart athletic flexible accessory 12 may be able to see wearer through camera of associated smart device while wearer trains, and may adjust posture, form, breathing, and the like, and may instruct wearer to stop if wearer looks wrong. Smart athletic flexible accessory 12 may have an electric shock feature so that if the wearer wants, a slight shock may be induced at the end for three more reps. Smart athletic flexible accessory 12 may have such electric shock feature for self-protection. In accordance with various embodiments, smart athletic flexible accessory 12 may be a pair of socks with sensors on the foot and ankle for leg resistance exercises. Such pair of socks may do all things that the gloves do, but for leg exercises.

Smart athletic flexible accessory 12 may have many uses. For example, smart athletic flexible accessory 12 may be used to see if workers, such as maids in a hotel or construction workers on a site, are working or not. Smart athletic flexible accessory 12 may be used for runners training to assess stride length and how hard their foot is hitting ground and how fast the runners are going, squats leg extensions, ballet, counting plie's and assessing jumping power.

Figure 2:
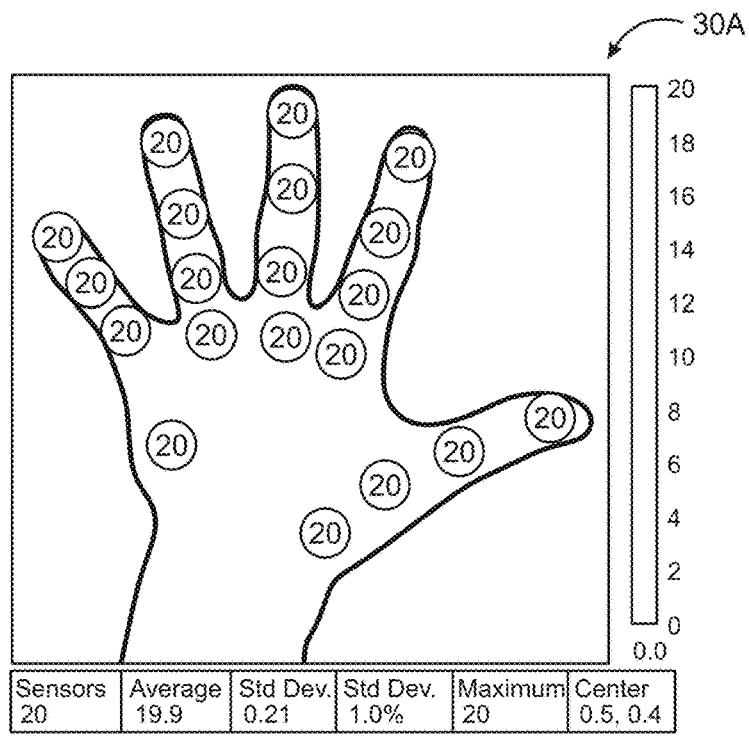
FIGS. 2 and 2A demonstrate two use cases, according to various embodiments described herein.
Figure 2A:
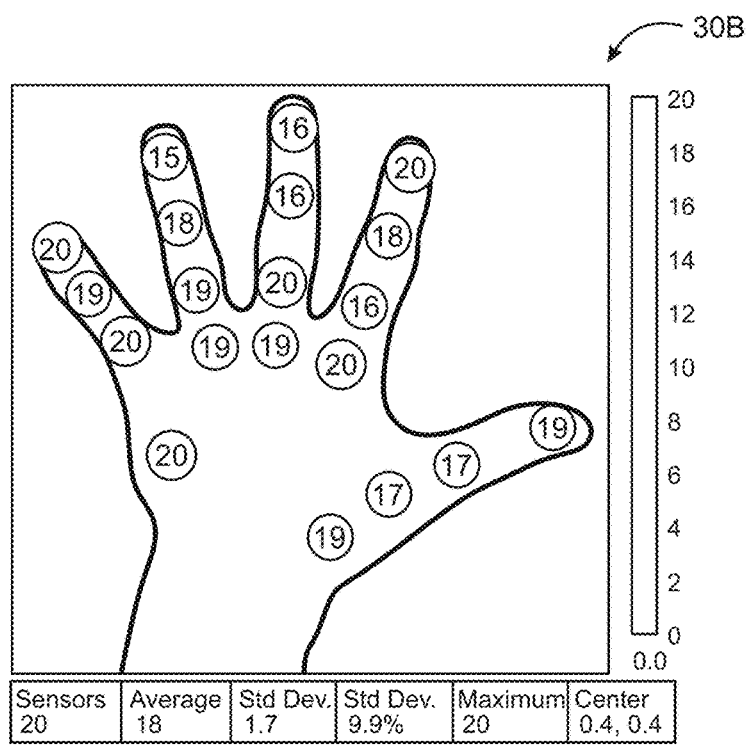

FIGS. 2 and 2A demonstrates two use cases, according to various embodiments described herein. In two use cases 30A and 30B demonstrated in FIGS. 2 and 2A respectively, there is shown an exemplary flexible glove as smart athletic flexible accessory 12 which can be of any color. There are shown plurality of fabric sensors 18 positioned on palm portion and extended appendages, indicated by circular buttons. Count of plurality of fabric sensors 18 may be 20 or 24 of 0.25"×0.25" sensor size. Additional sensors may be added on request. Material thickness may be 0.36 mm (0.014"). Calibrated pressure range may be 0-100 psi. It may be 30 psi using high pressure calibration jig (normally high pressure, or 100 psi performed at factory. Accuracy may correspond to a variation coefficient (which is standard deviation) less than 10% or approximately ±10 mmHg. In first use case illustrated in FIG. 2, there is shown an average pressure range of 20 psi measured by exemplary flexible glove having 20 sensors. Standard deviation is shown to be measured as 0.21 with a variation of 1.0%. Maximum sensor reading may be 20 psi and at center it may be 0.5, 0.4 psi. In second use case illustrated in FIG. 2A, there is shown an average pressure range of 12 psi down measured by exemplary flexible glove having 20 sensors. Standard deviation is shown to be measured as 1.77 with a variation of 9.9%. Maximum sensor reading may be 20 psi and at center it may be 0.4, 0.4 psi. It may be noted that first iteration may just count repetitions and linked to an app on electronic device 16. Possibly readout on flexible glove and rhythm pulse may show proper cadence as in 4 counts to lower and 2 with lift.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A performance improvement system, comprising:
   a smart athletic flexible accessory, wherein said smart athletic flexible accessory is a glove, a half finger glove or a without finger glove, embedded with said plurality of fabric sensors, said smart athletic flexible accessory comprising:
   a plurality of fabric sensors configured to measure data associated with a physical activity performed by a user; and
   a first transceiver configured to transmit said measured data, wherein said measured data corresponds to a measure of a weight that is being lifted and a lowering magnitude, wherein said measured data corresponds to a cadence for each repetition and an average for a plurality of repetitions for said physical activity; and an electronic device communicably coupled with said smart athletic flexible accessory, wherein said electronic device comprising:
- a second transceiver configured to receive said measured data from said smart athletic flexible accessory;
- a microprocessor configured to:
  - analyze said received data from said first transceiver;
    - generate a recommendation based on said analyzed data wherein said generated recommendation corresponds to one or more alternative physical activities that can be performed by said user, said generated recommendation facilitates improved grip strength; and
    - cause a display screen to display said generated recommendation.

2. The performance improvement system of claim 1, wherein said measured data corresponds to a time duration for which said weight is kept static.

3. The performance improvement system of claim 1, wherein said measured data corresponds to an average lifting time duration on each repetition of said physical activity.

4. The performance improvement system of claim 1, wherein said measured data is utilized to compensate a cadence, a resistance, a lowering, and an angle correction for said physical activity for optimal training purpose.

5. The performance improvement system of claim 1, wherein said smart athletic flexible accessory further comprising a program to identify said physical activity and adjust said measured data associated with said physical activity performed by said user, said program further indicates total weight lifted during each physical activity during each session.

6. The performance improvement system of claim 5, wherein said program further indicates grip strength and a point of failure of said grip strength.

7. The performance improvement system of claim 1, wherein said smart athletic flexible accessory further comprising a feedback circuitry configured to provide a feedback to said user to perform additional repetitions when said user is unable to perform additional repetitions, said feedback is a shock that uses electric stimulation.

8. The performance improvement system of claim 7, wherein said microprocessor is further configured to:
- analyze said additional repetitions;
- generate a new recommendation; and
- cause said display screen to display said generated new recommendation.

9. The performance improvement system of claim 1, wherein said smart athletic flexible accessory further includes a battery, said battery is a rechargeable battery, said battery is recharged via induction charging.

10. A performance improvement system, consisting of:
- a smart athletic flexible accessory, wherein said smart athletic flexible accessory is a glove, a half finger glove or a without finger glove, embedded with said plurality of fabric sensors, said smart athletic flexible accessory comprising:
  - a plurality of fabric sensors configured to measure data associated with a physical activity performed by a user; and
  - a first transceiver configured to transmit said measured data, wherein said measured data corresponds to a measure of a weight that is being lifted and a lowering magnitude, wherein said measured data corresponds to a cadence for each repetition and an average for a plurality of repetitions for said physical activity, said measured data further corresponds to a time duration for which said weight is kept static and an average lifting time duration on each repetition of said physical activity, said measured data is used to compensate a cadence, a resistance, a lowering, and an angle correction for said physical activity for optimal training purpose;
- an electronic device communicably coupled with said smart athletic flexible accessory, wherein said electronic device comprising:
  - a second transceiver configured to receive said measured data from said smart athletic flexible accessory;
  - a microprocessor configured to:
    analyze said received data from said first transceiver;
      generate a recommendation based on said analyzed data, wherein said generated recommendation corresponds to one or more alternative physical activities that can be performed by said user, said generated recommendation facilitates improved grip strength; and
      cause a display screen to display said generated recommendation;
- a program to identify said physical activity and adjust said measured data associated with said physical activity performed by said user, said program further indicates total weight lifted during each physical activity during each session, grip strength and a point failure of said grip strength; and
- a feedback circuitry configured to provide a feedback to said user to perform additional repetitions when said user is unable to perform additional repetitions, said feedback is a shock that uses electric stimulation.

* * * * *